(12) United States Patent
Vandenberg

(10) Patent No.: US 6,300,458 B1
(45) Date of Patent: Oct. 9, 2001

(54) HIGH MOLECULAR WEIGHT POLYMERS AND COPOLYMERS OF BHMDO FOR BIOMEDICAL APPLICATION

(76) Inventor: Edwin J. Vandenberg, 16223 Inca Ave., Fountain Hills, AZ (US) 85268

( * ) Notice: Subject to any disclaimer, the term of this patent is extended or adjusted under 35 U.S.C. 154(b) by 0 days.

(21) Appl. No.: 09/388,704

(22) Filed: Sep. 2, 1999

Related U.S. Application Data

(60) Provisional application No. 60/098,904, filed on Sep. 2, 1998.

(51) Int. Cl.[7] .................................................... C08G 64/00
(52) U.S. Cl. ............................................................ 528/196
(58) Field of Search .............................................. 528/196

(56) References Cited

FOREIGN PATENT DOCUMENTS

753704 * 2/1995 (JP).

* cited by examiner

Primary Examiner—Terressa M. Boykin

(74) Attorney, Agent, or Firm—Richard R. Mybeck

(57) ABSTRACT

Hydroxypolycarbonates (HPC) offer to the biomedical area hydroxyl functional polymers not now readily available to bind drugs, proteins, or carbohydrate polymers chemically or via hydrogen bonding to facilitate drug delivery and utility with subsequent biodegradability to acceptable byproducts. The cyclic carbonate (CC) from the monoketal diol of pentaerythritol polymerized in $CHCl_3$ at 60° C. with $Et_2Zn$ catalyst in $CHCl_3$ at 60° C. in 4 hours to a quantitative yield of high molecular weight, crystalline polymer (PCC), melt peak 199° C. and Tg of 99° C. PCC is readily hydrolyzed with 80% acetic acid to the water-insoluble but water-swollen HPC, poly[5,5-bis(hydroxymethyl)-1,3-dioxan-2-one], with $M_w=3.1\times10^4$. HPC degrades completely in vitro in <16 hours in PBS-1X buffer (Ph 7.4, 37° C.) to pentaerythritol and presumably $CO_2$. This rapid degradation rate is decreased with random copolymers of HPC with CC, ε-caprolactone, or $_L$-lactide. HPC and PCC may have important biomaterial applications as is and as the copolymers noted above or with ethylene oxide or other desirable comonomers. PCC and CC copolymers have properties attractive to the biomedical area as is or by conversion to the HPC product provided by hydrolysis or by in vivo enzymatic attack.

11 Claims, 2 Drawing Sheets

HIGH MOLECULAR WEIGHT POLYMERS AND COPOLYMERS OF BHMDO FOR BIOMEDICAL APPLICATION

This application is based upon United States Provisional Application Serial No. 60/098,904 filed Sep. 2, 1998. This invention was made with assistance from N.I.H. under contract IR 03RR1108401A1 and the United States government may have certain rights hereunder.

INTRODUCTION

The present invention relates to new high molecular weight polymers and copolymers of 5,5-bis (hydroxymethyl)-1,3-dioxan-2-one (herein referred to as "BHMDO") and to methods of making and using those polymers and copolymers in a number of biomedical applications including drug delivery systems and tissue engineering.

BACKGROUND OF THE INVENTION

The present invention relates to novel polymers having a wide range of biodegradability, biocompatibility, solubility, and physical morphology (e.g., crystalline, All amorphous, rubbery, or rigid). These unique polymers are synthesized from polycarbonates and polyiminocarbonates of carbohydrates, or analogous hydroxyl-containing, biocompatible moieties, such as pentaerythritol ("PE") or glycerin ("GLC").

BRIEF SUMMARY OF THE INVENTION

The present invention relates to high weight average molecular weight (>5,000) polymers and copolymers of 5,5-bis (bydroxymethyl) 1,3-dioxan-2-one (hereinafter referred to as "BHMDO") and processes for manufacturing these polymers and copolymers. These polymers are biocompatible and useful for a variety of biomedical applications. The homopolymer is unique compared to current biomedical polymers. It is crystalline and has a high melting point (ca 160–190° C.) which provides excellent mechanical properties. At the same time, they are hydrophilic and swellable by water (ca 100% at 37° C.), thereby enhancing biodegradability. The hydroxyl groups permit easy modification, an important advantage over non-hydrophilic biopolymers. For example, in the treatment of cancer, pain relief, or other therapy, one can chemically bond a drug by an appropriate hydroxyl group reaction to form a hydrolytically labile bond or with a small peptide link cleavable by body enzymes along with a chemically bonded polysaccharide or protein to target the desired cell with the appropriate drug. The hydroxyl groups provide hydrogen bonding with carbohydrate polymers, including nucleic acids, and proteins, which also facilitate direction of these polymers, as is or modified, to specific cites for therapeutic purposes. Properties can be varied widely via copolymers (generally from about 1% up to about 99% BHMDO) to change properties and permit diverse biomedical applications.

Accordingly, a principal object of the present invention is to provide new and improved hydroxyl functional polymers for facilitating the delivery and dissemination of medically useful drugs to the human system.

Another object of the present invention is to provide new high molecular weight polymers and copolymers of 5,5-bis (hydroxymethyl) 1,3-dioxan-2-one ("BHMDO") and methods of making such polymers.

A further object of the present invention is to employ new polymers and copolymers of BHMDO to provide a new and highly effective courier for delivery of therapeutic compounds to target sites.

These and still further objects as shall hereinafter appear are readily fulfilled by the present invention in a remarkably unexpected manner as will be readily discerned from the following detailed description of an exemplary embodiment.

DESCRIPTION OF THE PREFERRED EMBODIMENT

Figure 1A:
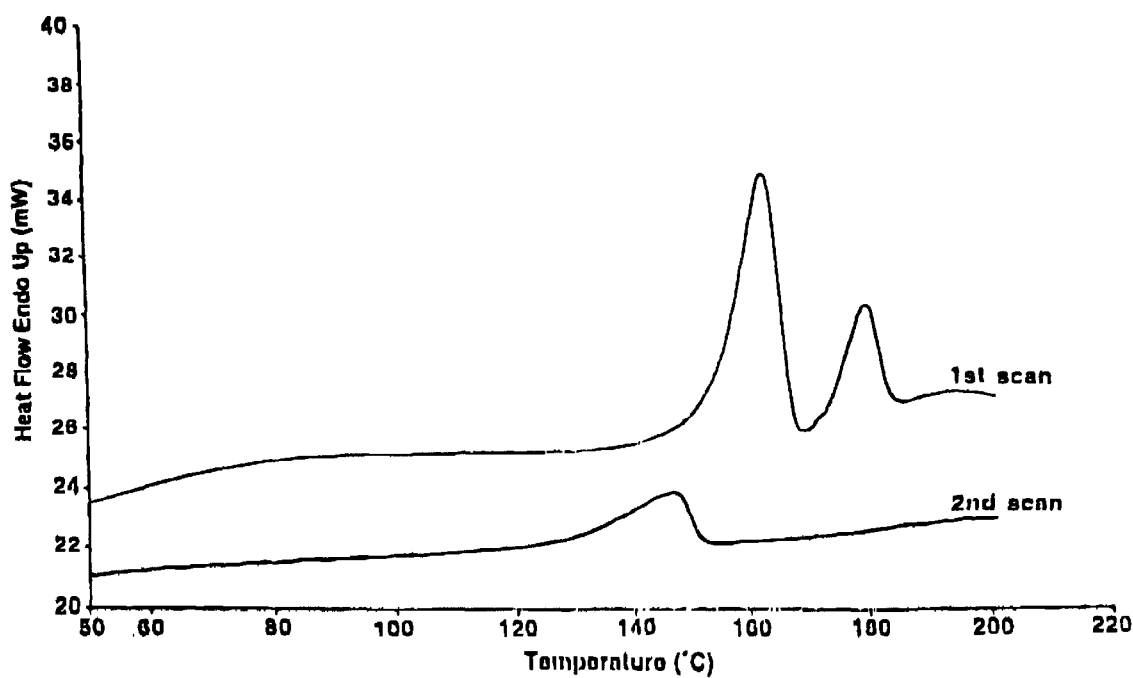
FIG. 1A, shows a typical DSC thermogram for HPC with no ketal.

In a preferred embodiment, 5,5-bis-(hydroxymethyl)-1,3-dioxan-2-one homopolymer (hereafter referred to as "hydroxy polycarbonate" or "HPC") is made from pentaerythritol by first blocking two hydroxyls with a group that is compatible with the final polymerization method, e.g., an acetal, ketal, formal or trimethylsiloxy replacement of the hydroxyl H. The remaining hydroxyls are then converted to a cyclic carbonate by appropriate reactions, such as with phosgene plus a base, or with ethyl chloroformate (1.1 mol per OH) plus a base, or with a dialkyl carbonate plus a base. This product is then purified and polymerized in bulk, in a solvent, such as $CHCl_3$-, or as a suspension in an inert organic diluent (e.g., toluene, n-heptane, and the like) using an organometallic catalyst, such as $Et_2Zn$, $R_2Zn$—$H_2O$, $R_3Al$—$H_2O$, and the like organometallic catalysts (where R is alkyl), organoalumoxanes, and aluminum alkoxides. The current preferred mode is reported below where the synthesis of HPC is shown in four steps.

Step 1

Preparation of 2,2-dimethyl-5,5-bis-(hydroxymethyl)-1,3-dioxane

Pentaerythritol (50 g, 0.36 mol) and p-toluenesulfonic acid monohydrate (0.61 g) were dissolved in 500 ml N,N-dimethylformamide (DMF, dried by molecular sieve at room temperature) at about 80° C., and then the mixture was allowed to cool undisturbed. When the solution cooled to about 40° C., stirring was started and 55.4 ml 2,2-dimethoxypropane (0.36 mol) was added. After 24 hours of stirring at room temperature, the solution was stirred at room temperature with 9.0 g of base treated DOWEX 1XZ-100 ion-exchange resin for 1 hour, filtered and then the solvent was evaporated under reduced pressure at 85° C. The base treated DOWEX 1XZ-100 ion exchange was prepared by washing 30 g. twice with 200 ml of deionized water, then washed with 300 ml of 4% aq. NaOH and then washed three times with 200 ml of water, filtered and then air-dried in a hood. After the treatment with this resin as noted above, the dry product was ground and extracted (Soxhlet), first with light petroleum ether (b.p. 40–60° C.) for 6 hours, then with diethyl ether for 12 hours, collected and dried. Yield: White crystals (40.0 g, 61.9%). M.P. 124.5°–125.5° C.; $1^1$H-NMR (300 MHz, DMSO-d6) 1.28 ppm (s, 6H), 3.34 ppm (d, J=5.7 Hz, 4H), 3.58 ppm (s, 4H), 4.47 ppm (t, J=5.4 Hz, 2H);

Step 2

Cyclic Carbonate (CC) From Product of Step 1

Triethylamine (70.6 ml, 0.501 mol) was added dropwise to a mixture of 2,2-dimethyl-5,5-bis-(hydroxymethyl)-1,3-dioxane (40.0 g, 0.0227 mol) and ethyl chloroformate (47.0 ml, 0.477 mol) dissolved in 1310 ml of tetrahydrofuran (THF) at 0° C. for over 30 minutes. The reaction mixture was stirred for 2 hours at 0° C., and then the precipitated triethylammonium chloride was filtered off, and the filtrate was concentrated under reduced pressure at 55° C. The residue was recrystallized from THF. White crystals were obtained. Yield: 27.2 g (59.3%), M.P. 155.5°–156.5° C.; $^1$H-NMR (300 MHz, CDCl$_3$) 1.44 ppm (s, 6H), 3.80 ppm (s, 4H), 4.31 ppm (s, 4H).

Step 3

Polymerization of CC from Step 2 to Polymerized Cyclic Carbonate (PCC)

Polymerizations were run under nitrogen in capped tubes with self-sealing rubber lined caps (Buna N or butyl rubber). Air was removed by nitrogen sparging of the closed vessel containing solid monomer for at least 20 minutes, and then solvent and catalyst solution were added via syringe. The containers were next tumbled in a constant temperature bath. Runs were usually short-stopped with anhydrous ethanol (1 ml per 10 ml solvent). Additional information on polymerization conditions, monomer to catalyst ratios, and monomer initial concentration are shown in Table 1 below. The resulting polymer was purified by precipitation from chloroform with methanol and dried under vacuum at room temperature: $^1$H-NMR (300 MHz, CDCl$_3$) 1.42 ppm (s, 6H), 3,77 ppm (s, 4H), 4.21 ppm (s, 4H).

The resulting product is poly[2,2-dimethyl-5,5-bis-(hydroxymethyl)-1,3-dioxane cyclic carbonate], referred to herein as "PCC". This product has biomedical applications in its own right based on its unique properties, as well as being useful to form the preferred copolymers of CC with cyclic esters, epoxides, lactides, glycolides, and the like compounds. PCC, when compared to HPC, has lower hydrophilicity, and higher glass transition temperatures (e.g., 101° C., first heat, and 68° C., second heat). PCC can be fabricated as a more rigid (higher modulus), amorphous film or prepared in crystalline form with a high melting point (peak M.P. 1 96° C. with end of melt of 202° C.) with greater durability and strength in vivo. PCC has a much higher molecular weight (probably 300,000–500,000) which will favor strength and durability applications and render it more stable to hydrolysis in vivo. A degradation test run on a fibrous sample in vitro (under the same conditions as described below in the "Biodegradability/biocompatibility Data on HPC") gave no apparent change after 16 hrs. at 37° C. There was no loss in weight, $^1$H-NMR was unchanged and $\eta_{inh}$ viscosity (0.3% CHCl$_3$, 30° C.) was changed little from an initial 1.90 to 1.74. Thus, PCC was found to be far more stable than the hydroxy polycarbonate ("HPC").

Step 4

Deacetalization of PCC from Step 3 to form Hydroxy Polycarbonate (HPC)

1 g polymer dissolved in 100 ml CHCl$_3$ and 33 ml of 80% acetic acid were mixed and stirred at room temperature overnight. Then 67 ml 80% acetic acid was added into the mixture, which was then refluxed in a 85° C. oil bath for 1 hour. The resulting polymer was recovered by evaporation of the volatile components under reduced pressure below 70° C., and further air-dried in a hood overnight. It was washed with pH 6.0 buffer, then water washed and dried in vacuo at room temperature. Yield: 100%, $^1$H-NMR (300 Mhz, DMSO-d6): 3.36 ppm (d, J=5.7 Hz, 4H), 4.04 ppm (s, 4H), 4.68 ppm (t, 3=5.3, 2H), $\eta_{inh}$ (DMAC, 30° C.) 0.3 and a weight-average molecular weight of $3.1 \times 10^4$ when its $\eta_{inh}$ is 0.31 in DMSO at 30.0° C.

Scheme 1
Synthesis of poly(5,5-bis-(hydroxymethyl)-1,3-dioxan-2-one) ("HPC")

STEP 1

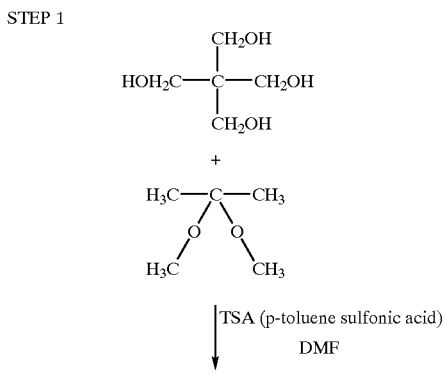

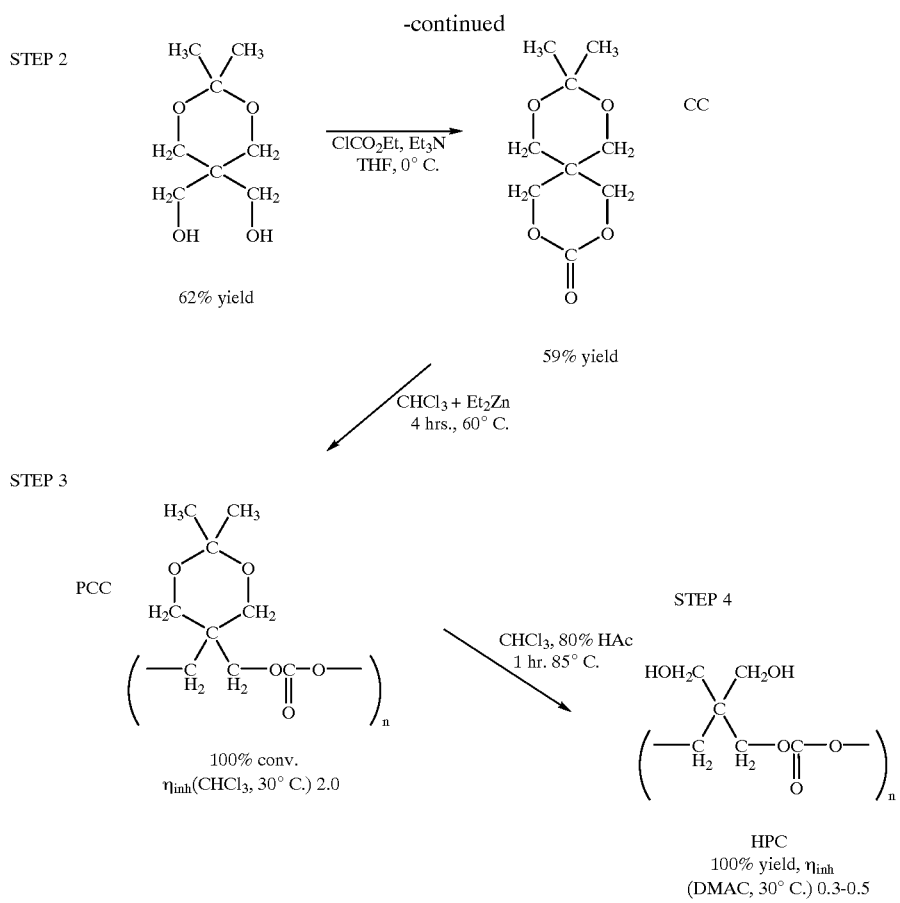

A wide variety of useful copolymers of CC as is or after deprotection to give HPC units with about 1–99% comonomer can be readily made using the teachings of this disclosure.

carbonates from glycerin (1,3 carbonate), glycidol, 3-hydroxyoxetane, 3,3-bis (hydroxymethyl) oxetane, methyl (or ethyl)-3-hydroxymethyl oxetane, and 1,4-dihydroxy-2, 3-epoxybutane. Simple epoxides, such as ethylene oxide,

TABLE 1

Ring-Opening Polymerization of CC by Different Catalysts in Solution or in Bulk[a]

| entry | catalyst | solvent | monomer concn (g/mL) | temp (° C.) | time (h) | monomer conversion[b] (%) | $\eta_{inh}$[c] (dL/g) |
|---|---|---|---|---|---|---|---|
| 1 | IBAO | toluene | 20 | 80 | 17 | 100 | 0.34 |
| 2 | IBAO | bulk | | 180 | 3 | 83 | 0.19 |
| 3 | IBAO-0.50AA | toluene | 20 | 80 | 42 | 59 | 0.06 |
| 4 | IBAO-0.50AA | bulk | | 180 | 3 | 73 | 0.20 |
| 5 | $^{i}Bu_3Al$—0.5$H_2O$—6.0$Et_2O$ | toluene | 20 | 80 | 24 | 100 | 0.30 |
| 6 | $^{i}Bu_3Al$—0.5$H_2O$—6.0$Et_2O$ | $CHCl_3$ | 20 | 60 | 18 | 74 | 0.15 |
| 7 | $Et_3Al$—0.6$H_2O$-0.5AA-2THF | $CHCl_3$ | 20 | 60 | 18 | 68 | 0.15 |
| 8 | $Et_2Zn$ | $CHCl_3$ | 20 | 60 | 4 | 100 | 0.95 |

[a]Monomer-to-catalyst ration ($[M]_0/[C]_0$) was 76 mol/mol; $[C]_0$ was taken as the moles of [Al] or [Zn].
[b]Determined by $^1H$ NMR.
[c]Inherent viscosity, $\eta_{inh}$, was determined in $CHCL_3$ at 30.0° C.

PCC and CC copolymers have the unique advantage that the ketal units can be converted in vitro, and potentially in vivo by enzyme attack, to hydroxyl groups which can advantageously acquire hydrophilic properties and hydrogen bond to carbohydrate and protein units. Monomers which contain free hydroxyl radicals and whose copolymers are made by the same general procedure as above include cyclic propylene oxide, and other alkylene oxides also provide useful copolymers including random, block and graft types. Ethylene oxide copolymers are particularly useful to provide biocompatible, water-soluble, or higher water-swell products (with or without deprotection) for a variety of applications where water solubility or higher water swelling is needed or desirable. Other cyclic carbonates, preferably those with six-member rings, are useful as comonomers, such as trimethylene carbonate, 2,2-dimethyltrimethylene carbonate, 5-methylene-1,3-dioxan-2-one, 1,3-dioxepan-2-one, or cyclic esters such as δ-valerolactone, ε-caprolactone, β-butyrolactone, β-propiolactone, lactides, and glycolides. Copolymers from 4-member cyclic-esters as β-hydroxybutyrate are also useful.

Effect of Monomer Concentration, Polymerization Temperature, and Solvent on the Ring-Opening Polymerization of CC (Table 2)

For IBAO-catalyzed polymerization (see: entries 1–3), the initial monomer concentration has almost no effect on the final polymer inherent viscosity when the polymerization was conducted at 65° C., but the polymer yield rapidly decreased at higher initial monomer concentration (40%), with the same 17 hours polymerization time. Higher polymerization temperature increased the inherent viscosities from 0.29 to 0.34 and 0.80 when the polymerization temperature was increased from 65 to 80 and 90° C., respectively (see: entries 2, 4, and 5). Contrary to the lower polymerization temperature results, the inherent viscosity increased with the initial monomer concentration at 90° C.; e.g., $\eta_{inh}$ increased from 20% to 50% in toluene (see: entries 5 and 6). Comparing entries 6 and 7 at the same polymerization conditions, 50% monomer concentration, and 90° C. $Et_2Zn$ increased $\eta_{inh}$ from 1.03 to 1.61 compared to the case of IBAO. For $Et_2Zn$-catalyzed polymerization, $\eta_{inh}$ increased with monomer concentration in 1,1,2,2-tetrachloroethane at 80° C. or in chloroform at 60° C. (see: entries 8–11). Different solvents have a different effect on $\eta_{inh}$ (see: entries 7–11). These data indicate that chloroform is the best solvent with a higher inherent viscosity of 1.15, at a lower temperature (60° C.) and shorter reaction time (4 hours) compared to the case of toluene (see: entry 7) or 1,1,2,2-tetrachloroethane (see: entry 9).

mer conversion was complete, the molecular weight decreased with time if the polymerization was not stopped. $^1$H NMR analyses of these samples showed that no ether linkages can be detected, which indicates no decarboxylation reaction even after keeping the "active" polymerization for 17 hours. Transesterification is only one reasonable explanation for the decrease of inherent viscosity after complete monomer conversion.

TABLE 3

Effect of Time on the Polymerization of CC at 50% Concentration Catalyzed by $Et_2Zn$ at 60° C. in Chloroform[a]

|   | monomer concn (g/mL) | time (h) | monomer conversion[b] (%) | $\eta_{inh}$[c] (dL/g) |
|---|---|---|---|---|
| 1 | 50 | 2.17 | 87 | 1.57 |
| 2 | 50 | 3.00 | 92 | 2.16 |
| 3 | 50 | 3.25 | 100 | 2.29 |
| 4 | 50 | 3.50 | 100 | 1.90 |
| 5 | 50 | 4.00 | 100 | 1.51 |
| 6 | 50 | 17.00 | 100 | 1.01 |

[a]Monomer-to-catalyst ration ($[M]_0/[C]_0$) was 76 mol/mol; $[C]_0$ was taken as the moles of [Al] or [Zn].
[b]Determined by $^1$H NMR.
[c]Inherent viscosity, $\eta_{inh}$, was determined in $CHCL_3$ at 30.0° C.

Deketalization of PCC

Removal of the hydroxyl ketal blocking groups was carried out 80% acetic acid in a chloroform medium, with a 100% yield. The ketal protons at δ=1.42 ppm have completely disappeared, whereas correspondingly the singlets at δ=4.20 ppm (Ha1) and 3.77 ppm (Hb1) of the precursor PCC have been shifted to higher fields (singlet at δ=4.04 ppm (Ha2) and doublet at 3.36 ppm (Hb2), which is clear evidence for the completeness of the deketalization reaction. Furthermore, a triplet for the hydroxyl protons has appeared

TABLE 2

Effect of Monomer Concentration, Polymerization Temperature, and Solvent on the Ring-Opening Polymerization of CC[a]

| entry | catalyst | solvent | monomer concn (g/mL) | temp (° C.) | time (h) | monomer conversion[b] (%) | $\eta_{inh}$[c] (dL/g) |
|---|---|---|---|---|---|---|---|
| 1 | IBAO | toluene | 10 | 65 | 17 | 100 | 0.26 |
| 2 | IBAO | toluene | 20 | 65 | 17 | 100 | 0.29 |
| 3 | IBAO | toluene | 40 | 65 | 17 | 30 | 0.22 |
| 4 | IBAO | toluene | 20 | 80 | 17 | 100 | 0.34 |
| 5 | IBAO | toluene | 20 | 90 | 17 | 100 | 0.80 |
| 6 | IBAO | toluene | 50 | 90 | 17 | 97 | 1.03 |
| 7 | $Et_2Zn$ | toluene | 50 | 90 | 17 | 98 | 1.61 |
| 8 | $Et_2Zn$ | $Cl_2CHCHCl_2$ | 20 | 80 | 2 | 96 | 0.51 |
| 9 | $Et_2Zn$ | $Cl_2CHCHCl_2$ | 50 | 80 | 2 | 97 | 0.90 |
| 10 | $Et_2Zn$ | $CHCl_3$ | 20 | 60 | 4 | 100 | 0.95 |
| 11 | $Et_2Zn$ | $CHCl_3$ | 50 | 60 | 4 | 100 | 1.51 |

[a]Monomer-to-catalyst ration ($[M]_0/[C]_0$) was 76 mol/mol; $[C]_0$ was taken as the moles of [Al] or [Zn].
[b]Determined by $^1$H NMR.
[c]Inherent viscosity, $\eta_{inh}$, was determined in $CHCL_3$ at 30.0° C.

Effect of Polymerization Time on the Ring-Opening Polymerization of CC

Table 3 shows the effect of polymerization time on the polymerization of CC catalyzed by $Et_2Zn$ at 60° C. in chloroform with a CC to Zn molar ratio of 76 and 50%o (g/mL) initial $CC/CHCl_3$ concentration. The polymerization was fast, giving 87% monomer conversion at 2 hours 10 min and 100% at 3 hours 15 minutes. The inherent viscosity increased with monomer conversion. However, after monoat 67 4.68 ppm (Hd), and the intensity ratio of protons Ha2, Hb2, and Hd is very close to 2:2:1 with a good agreement with theoretical values within the limits of the NMR experimental error. Thus, aliphatic polycarbonates bearing hydroxyl pendant groups, poly-[5,5-bis(hydroxymethyl)-1,3-dioxan-2-one] (HPC, Scheme 1), were successfully prepared, which opens new application prospects. This new functional aliphatic polycarbonate is not soluble in chloroform, THF, acetone, methanol, toluene, etc., but soluble in DMSO, DMF, and DMAC. It is completely dissolved in water only at higher temperature, i.e., above 70° C., with complete degradation based on $^1H$ NMR. The inherent viscosity is lower if compared with its precursor. For example, $\eta_{inh}$ are between 0.12 and 0.35 in DMSO at 30.0° C., corresponding to the precursor PCC with $\eta_{inh}$ between 0.80 and 2.3 in $CHCl_3$ at 30.0° C. Inherent viscosities are not directly comparable because of their different polymer structures and the different solvent systems for $\eta_{inh}$ measurement. Laser light scattering Zimm analysis shows that the weight-average molecular weight ($M_w$) is $3.1 \times 10^4$ for HPC in molecular sieve dried DMF at ambient temperature when its $\eta_{inh}$ is 0.31 in DMSO at 30.0° C. It is believed that the precursor PCC is of much higher molecular weight.

Crystalline Properties

Figure 1B:
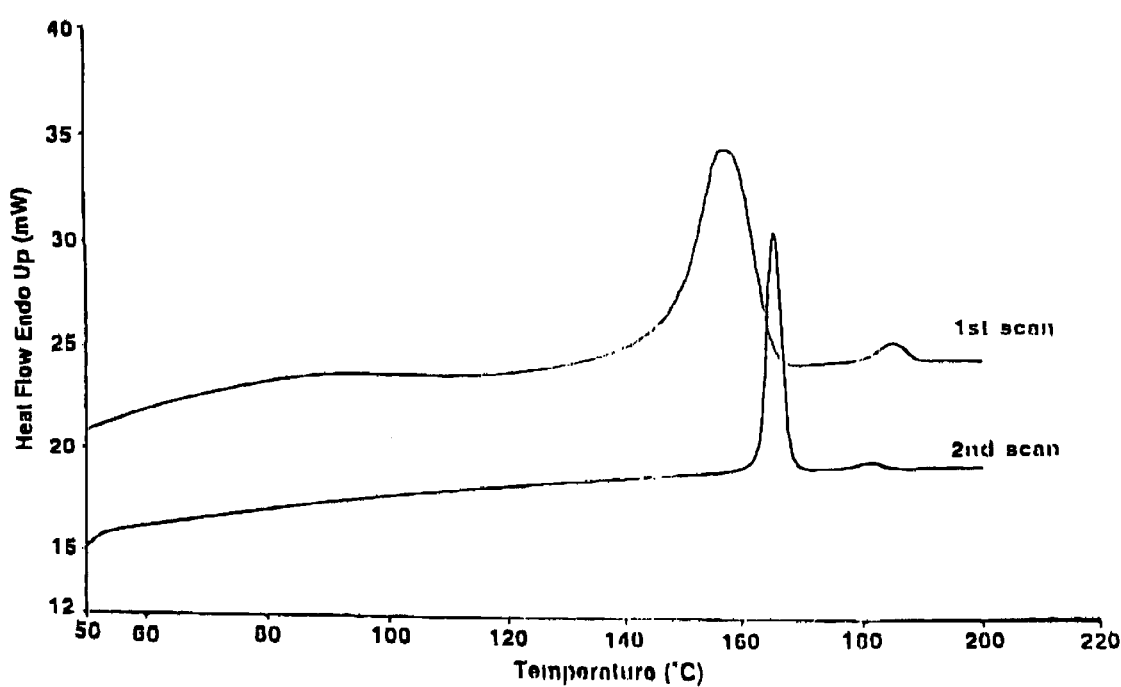
FIG. 1B, shows a typical DSC thermogram for 98% HPC and 2% (w/w) ketal protected groups.

The crystalline properties of PCC and HPC were analyzed by differential scanning calorimetry (DSC). All the thermal properties are listed in Table 4. A typical DSC thermogram for HPC is shown in FIG. 1A with no ketal and in FIG. 1B with 2% ketal, HPC-98. For PCC, the melting peak is quite sharp ($T_m$) and is quite high, i.e., 199° C., and the melting enthalpy ($\Delta H_m$) is high at 45.1 J/g. No crystallization from the melt occurs even when the cooldown from the melt is at a rate of 10° C./min to room temperature, followed by a reheat cycle. The glass transition temperature ($T_g$) of PCC is also quite high, though it dropped from 99° C. for crystalline sample to 68° C. for amorphous sample. Clearly, high crystallinity with high melting temperature and glass transition temperature of PCC is a big improvement over the current aliphatic polycarbonates, such as PTMC ($T_g = -20°$ C., $T_m = 36°$ C., $\Delta H_m = 7$ J/g) and PDTC ($T_g = 27°$ C., $T_m = 108°$ C., $\Delta H_m = 20$ J/g), etc. After deketalization, the polymers still retain high crystallinity and a high melting temperature, but two melting endotherm peaks were found for the first heat of HPC (FIG. 1A). The melting temperature of HPC is lower somewhat compared to that of PCC. After fast cooling of the HPC from meltdown to room temperature at a rate of 50–100° C./min and heating again, a substantial melting endotherm was detected (24% of the total first heat melt peaks), which suggests a faster crystalline rate of HPC compared with that of its precursor PCC. For the second scan, both samples (HPC and HPC-98) showed one melting endotherm peak (FIG. 1A,B), but the HPC-98 peak was sharper and at about 20° C. higher temperature compared to that of HPC. This difference might result from their different molecular weight and/or because one sample contained 2% protected groups (Table 4). No $T_g$ could be detected for HPC at the experimental temperature range (50–200° C.) studied.

TABLE 4

DSC Data for PCC and HPC

| sample | $\eta_{inh}$ (dL/g) | $T_g$ (° C.) | $T_m{}^b$ (° C.) first scan | $\Delta H_m$ (J/g) |
|---|---|---|---|---|
| PCC | 2.29 | 99 | 199 | 45.1 |
| HPC | 0.19 |  | 163; 179 | 41.8; 12.4 |
| HPC$^a$ | 0.31 |  | 157; 185 | 55.7; 2.0 |
|  |  |  | second scan |  |
| PCC | 2.29 | 99 | 199 | 45.1 |
| HPC | 0.19 |  | 163; 179 | 41.8; 12.4 |
| HPC$^a$ | 0.31 |  | 157; 185 | 55.7; 2.0 |

$^a$This sample contains 2% ketal protecting groups.
$^b$Melt peak.

Polymer in Vitro Degradation Test

The in vitro degradation test was carried out by immersion of the powder form of the polymer in phosphate-buffered saline (PBS-1X), pH=7.4 at 37° C., with agitation under nitrogen. The samples were recovered periodically, and their $\eta_{inh}$ and weight loss data are summarized in Table 5. For the protected polycarbonate, PCC, no gravimetric weight loss was detected after 16 hours, while its $\eta_{inh}$ decreased somewhat. For the completely deprotected polymer, HPC, the rate of hydrolytic polymer chain cleavage was very rapid, so that after 16 hours there was no water-insoluble HPC left. $^1H$ NMR of the 16 hour solution showed that only pentaerythritol was detectable. The expected coproduct, $CO_2$, was not checked for. After the 1 hour degradation period, the inherent viscosity of HPC decreased 21.4%; meanwhile, its weight loss was 50.8%. These results confirmed that hydroxyl pendant groups improve the hydrophilicity of polycarbonates chains and enhance its hydrolytic degradability.

TABLE 5

In Vitro Degradation Test in PBS-1X* Buffer$^a$

| sample | time (h) | $\eta_{inh}$ (dL/g) before test | $\eta_{inh}$ (dL/g) after test | wt loss (%) |
|---|---|---|---|---|
| PCC | 16 | 1.90 | 1.74 | 0 |
| HPC | 1 | 0.14 | 0.11 | 50.8 |
| HPC | 2 | 0.14 | 0.05 | 55.0 |
| HPC | 4 | 0.14 |  | 77.5 |
| HPC | 16 | 0.14 |  | 100 |
| HPC-65$^b$ | 16 | 0.19 | 0.17 | 42.9 |
| HPC-CL$^c$ | 16 | 0.35 | 0.16 | 58.3 |

*phosphate-buffered saline, product of Boehringer-Manheim
$^a$For PCC, $\eta_{inh}$ was determined in $CHCl_3$ at 30.0° C.; all the other samples were determined in DMSO at 30.0° C.
$^b$65% deketalization of PCC.
$^c$HPC-CL: copolymer of HPC and ε-caprolactone (CL) containing 17.5% of CL repeat unit.

The partial (65%) deketalization of PCC (HPC-65 in Table 5), prepared by a milder deketalization treatment, decreased the hydrolysis rate compared with the case of HPC. As Table 5 shows, HPC-65 only lost 10.5% of $\eta_{inh}$ and 42.9% of weight over the 16 hours degradation period, but at the same conditions, the complete deketalization sample (HPC) was completely decomposed. $^1H$ NMR analysis indicated that, after immersion of HPC-65 in phosphate-buffered saline at 37° C. for 16 hours, the ketal content increased from 35% (before test) to 68% (after test). This result indicates that the deketalization is not a random one; i.e., after one chain unit is deprotected, the adjacent ketal unit is deprotected next. Eventually, the HPC blocks break up by an unidentified process to give pentaerythritol and $CO_2$.

Aliphatic Carbonate and Ester Copolymers of CC and Their in Vitro Degradation

Copolymerization is known to provide new materials, whose properties are often the average of those of the parent homopolymers. This is a valuable method to finely tune one property to the value needed for a specific application. Preliminary copolymerizations of CC with ε-caprolactone (CL) or $_L$-lactide (LA) were made using $Et_2Zn$ catalyst in $CHCl_3$ at 60° C. (Table 6). For copolymerization of CC with CL, the copolymers yield a quite high inherent viscosity after 16 hours reaction with a high comonomer conversion. Copolymerization of CC with LA was not complete after 48 hours reaction, and the inherent viscosity of the copolymer is lower (see: entry 3). The compositions of the copolymers totally depend on the commoner feed ratio and were in a good agreement with their charge composition within the limits of NMR experiment errors, indication very favorable copolymerization. Table 7 shows $^{13}C$ NMR data on the CC/CL copolymer peaks at the carbonyl region in $CDCl_3$. Clearly, $^{13}C$ NMR analysis confirmed copolymer formation.

TABLE 6

Ring-Opening Copolymerization of CC with ε-caprolactone (CL) and with L-Lactide (LA) in Chloroform at 60° C. with $Et_2Zn$ Catalyst[a]

| | | | conversion[c] | | | Fcc[e] | |
|---|---|---|---|---|---|---|---|
| comonomer | fcc[b] | time (h) | CC | comonomer (%) | $\eta_{inh}$[d] (dL/g) | theor | exp |
| CL | 0.83 | 16 | 91.1 | 100 | 2.57 | 0.820 | 0.826 |
| CL | 0.17 | 16 | 100 | 100 | 1.08 | 0.170 | 0.175 |
| LA | 0.83 | 48 | 92.6 | 72.9 | 0.12 | 0.864 | 0.892 |

[a]Monomer-to-catalyst ratio ($[M]_0/[C]_0$) was 76 mol/mol; initial total monomer concentration was 50%.
[b]Molar fraction of CC in the feed.
[c]Determined by $^1H$ NMR.
[d]$\eta_{inh}$ was determined in $CHCl_3$ at 30.0° C.
[e]Molar fraction of the CC repeating units in the copolymer.

TABLE 7

Chemical Shift of PCC, PCl, and CC/CL Copolymer at Carbonyl Region by $^{13}C$ NMR

| polymer | FCC[a] | FCL[b] | δ(ppm) |
|---|---|---|---|
| PCC | 1.0 | 0 | 154.7 |
| P(CC-Co-CL) | 0.826 | 0.174 | 154.7, 154.8, 155.0, 173.0 |
| P(CC-Co-CL) | 0.175 | 0.825 | 154.8, 155.1, 173.1, 173.5 |
| PCL | 0 | 1.0 | 173.5 |

[a]FCC: molar fraction of the CC repeating units in the copolymer.
[b]FCL: molar fraction of the CL repeating units in the copolymer Deacetalization of these copolymers has also been successfully performed with 80% acetic acid in a chloroform medium, with a 100% yield. The in vitro degradation test of HPC-$c_0$-CL) ($F_{CL}$=0.17) was also carried out by immersion of powder form (see: Table 6, entry 2) in phosphate-buffered saline (pH=7.4) at 37° C. with stirring under nitrogen. This sample lost 54.3% $\eta_{inh}$ and 58.3% weight over 16 hours. As expected, the degradation rate of HPC can be adjusted by introducing ε-caprolactone units into the HPC polycarbonate chains via random copolymerization.

Thus, a ketal-protected aliphatic cyclic carbonate, CC, was synthesized from pentaerythritol. This new monomer was successfully ring-opening polymerized in solution using various organometallic catalysts, such as isobutylalumoxane and $Et_2Zn$. Polymerization in chloroform at 60° C. catalyzed by $Et_2Zn$ was preferred for the synthesis of high molecular weight PCC. After complete monomer conversion, an increase in polymerization time decreases polycarbonate molecular weight, probably due to transesterfication reaction. This new monomer can copolymerize with ε-caprolactone or $_L$-lactide. Deketalization of PCC or copolymers of CC was achieved with 100% yield in 80% acetic acid and chloroform medium. Therefore, aliphatic polycarbonates bearing hydroxyl pendant groups (HPC) can be easily prepared. The ketal-protected aliphatic polycarbonates (PCC) and the new hydroxy polycarbonate (HPC) are high crystallinity polymers with high melting temperature, i.e., 199° C. for PCC and 163–179° C. for HPC. This is a unique property compared with current aliphatic polycarbonates. The advantage of the novel hydroxy aliphatic polycarbonate, HPC, is that its hydroxyl pendant groups permit attachment of desirable entities to the biodegradable main chain, such as therapeutic agents, proteins, or carbohydrate polymers, to enhance biomedical activity. In vitro degradation test showed that the degradation rate of HPC is fast, and this rate can be decreased by the partial deketalization of PCC or copolymerization with ε-caprolactone or $_L$-lactide. On the other hand, PCC was very stable in the same in vitro degradation test. The unusual hydrolytic stability and the interesting physical properties of PCC suggests a variety of biomedical applications. Also, PCC or CC copolymers may be hydrolyzed in vivo by enzymatic attack to confer some of the possible advantages of HPC and its copolymers.

An other intriguing possibility is that CC copolymers with ethylene oxide (EO) may be especially useful products before or after deprotection to provide copolymers varying from water-insoluble but swellable to water-soluble depending on composition and with increasing hydrolytic stability. Such products should be biocompatible, at least in the deprotected form, since PEO is currently approved as biocompatible by the FDA. Previously, EO was found to give a unique epichlorohydrin copolymer for elastomer applications and may be unique here, partly because of its low molecular weight and water solubility of its polymers.

Other CC copolymers with monomers that form biocompatible homopolymers include ε-caprolactone, $_L$-lactide, glycolide, trimethylene carbonate, and β-hydroxybutyrate.

Comonomers which introduce carboxylic acid anhydride units in the chain, for example using cyclic dimers from dicarboxylic acids as malonic and succinic acids, are also useful. For some applications, the use of a cross-linking agent which gives biocompatible degradation products is desirable to decrease solubility, increase molecular weight and/or enhance some mechanical properties. The biscarbonate of pentaerythritol (hereinafter referred to as "PE") is such an agent. A further application of this agent would be to prepare the main polymer with hydroxyl end groups and then react them with the bis carbonate in the fabrication step with an appropriate catalyst to yield a simplified process, improved ease of fabrication, and improved properties.

Other cyclic monomers will yield useful copolymers; for example, D,L-lactide (or the meso D,L, the DD or LL isomers), glycolide, ε-caprolactone, pivalolactone, α or β-butyrolactone, 2-cyano-2-methyl trimethylene carbonate, trimethylene urethane, or oxetane. An iminocarbonate of PE, analogous to BHMDO in which the C=O is replaced with a C=NH, will also yield useful copolymers.

Random, block, and graft copolymers are envisioned and are projected for use for specific applications, depending on properties desired.

The PCC polymer of the protected BHMDO can be made by appropriate choice of catalyst and conditions followed by polymerization, after purification as needed, in the fabrication step and then deprotection, if desired, for an improved product (HPC).

The protected monomer is also useful as the desirable comonomer units made by copolymerization or by incomplete deprotection of the initial protected polymer.

Appropriate catalysts for the polymerization of the cyclic carbonates and copolymerizing the cyclic comonomers include: Li alkyls (sec.-BuLi), Al alkoxides [Al-(Osec-Bu)$_3$], Al(acetylacetonate)$_3$, Al-(OiPr)$_3$, $R_2$AlOR (R=Et), organoaluminums, alumoxanes, $R_2$Mg (R=n-Bu), organo Sn compounds as $Bu_2$Sn (OMe)$_2$, $Bu_2$SnO, $BuSnCl_3$, $R_2$Zn (R=Et), and other compounds known to be analogous thereto.

Carbon dioxide copolymers of protected 3,3-bis (hydroxymethyl) oxetane ("BHMO") or related 3-methyl- 3-(hydroxymethyl)oxetane ("MHMO"), 3-ethyl-3-(hydroxymethyl)oxetane ("EHMO"), and bis(hydroxymethyl)ethylene oxide (e.g., an alternative approach to BHMDO and related products) are promising biomedical materials, as is or after deprotection or as copolymers with the monomers previously cited. The $CO_2$ copolymers can be made by means of catalysts used for expoxide-$CO_2$ copolymers [e.g., $R_2Zn$—$H_2O$ (or other polyreactive agents in place of $H_2O$), $R_3Al$ or $R_2Mg$ reaction product catalysts].

Other uses for the products of this invention include polymer-bound drugs and mixtures with drugs to be implanted or used at the point of need, thereby providing a slow release over a period of time.

An alternative synthesis to prepare the products of this invention is to react the diol from Step 1:

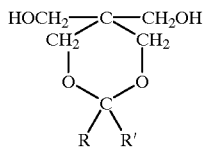

wherein R and R'=alkyl, cycloalkyl, aryl, arylalkyl, and derivatives thereof and hydrogen, etc., R and R'may be the same or different and then react with $COCl_2$ (or a dimer or trimer thereof) in the presence of base to give a polycarbonate or react with $R_2\ CO_3$ and an ester interchange catalyst (where R can be alkyl, aryl, and the like) while removing the volatile ROH product to form the polycarbonate or cyclic carbonate. Thus, a polycarbonate can be the direct product of the $COCl_2$ reaction or can give cyclic carbonate which is polymerized to the polycarbonate:

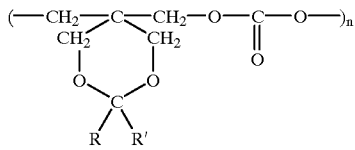

and the blocking group (CRR') can be removed as shown in Step 4 to yield HPC.

Biodegradability/biocompatibility Data on HPC 0.020 g. HPC in powder form was placed in 7 ml. of pH 7.4 PBS 1×buffer (0.001 M $KH_2PO_4$, 0.01 M $Na_2HPO$, 0.137 M NaCl, and 0.0027 M KCl in highly purified distilled water) under nitrogen and rotated in a 37° C. water bath. After 16 hours, the polymer was completely dissolved and remained in solution at room temperature or lower. $^1$H-NMR indicated that the polymer is completely decomposed to pentaerythritol (and also $CO_2$ whose formation was not verified) and no other detectable products. Shorter reaction times were visually checked and it was estimated that after 4 hours at 37° C., a major portion (e.g., 50–75%) of the HPC had dissolved (degraded). This data shows that the HPC degrades rapidly when exposed to near body conditions. If the HPC was in a more solidified form (e.g., film or fiber), it would surface erode somewhat more slowly. The data indicates that HPC will be useful in those applications where the polymer is readily absorbable to non-toxic products. A promising application is to mix the polymer with an anti-cancer drug and implant near a cancer such as a brain tumor, to destroy the cancer cells. Cancer of the lung, liver, colon, ovaries and similarly vulnerable human organs are equally viable targets.

The rate of hydrolysis and/or biodegradation of the biomedical polymer can be controlled and specifically reduced to fit the drug—cancer relationship by various means such as copolymers (shown in Table 5 above) for HPC-65 and HPC-CL.

The biodegradable and biocompatible polymers of the present invention open still another avenue of human therapy in that they are useful in tissue engineering. A scaffold of the biodegradable polymers is created and cells of body parts, eg., ears, liver, lung, skin and the like can be grown thereon until the desired part is recreated. The part is then transplanted into humans where the cells link in with existing living cells and the scaffold disintegrates leaving only the bonded cells to thrive.

To further illustrate the present invention, the following Examples are presented.

EXAMPLE 1

A viscous solution (20–30%) in dimethyl formamide (DMF) of a 20–80 HPC-PCC copolymer prepared by controlled hydrolysis of PCC plus 10% lidocaine (based on the polymer) was added and the solution spun into a fiber into $H_2O$, water washed and dried. The dry fiber was then used to make a fibrous mat which can be placed in a wound before closure to reduce pain during healing. The dry fiber can also be used as a suture without lidocaine or can be made with other compositions of HPC or PCC. Lidocaine is a currently used anesthetic and its chemical name is: 2(diethylamino-N-(2,6-dimethyl phenyl) acetamide.

EXAMPLE 2

Another application of the present invention comprises development of erodible yet biocompatible materials with desirable mechanical properties could be useful in many applications such as a temporary replacement for bone. The polymers HPC and PLC may also be attractive materials for temporary scaffolds and barriers, such as sutures (qv), bioabsorbable prostheses, and vascular grafts. They may also be useful as biodegradable plastics for bottles or bags. A feature of these polymers is their tendency to undergo surface erosion. Heterogeneous hydrolysis theoretically would better preserve the mechanical strength and physical integrity of the matrix during biodegradation, which is highly desirable in terms of predictable performance. The types of drugs that can be released from HPC and PLC include anticancer drugs, angiogenesis inhibitors, antifibroblastic agents, and hormones. The antitumor drug bischloronitrosourea in L1210 leukemia and 9L gliosarcoma models inhibit neovascularization as a means of controlling tumor growth. A combination of cortisone and heparin, known angiogenesis inhibitors, mixed with HPC or PCC retard the growth of the tumor. To improve insulin delivery, insulin can be incorporated into HPC or PCC microspheres of different compositions. These microspheres, when implanted subcutaneously into diabetic rats, controlled urine glucose level and controlled serum glucose.

EXAMPLE 3

Best uniform drug delivery is obtained via surface degradation with a fairly hydrophobic polymer. Thus, HPC-PCC copolymers or HPC—coprolactone (CL) copolymer should be preferably 70–80% of the hydrophobic monomer (PCC or CC). Alternatively, protecting groups of PCC can be made with a ketone of a long chain (7–15 C) hydrocarbon or a cychoalkyl ketone (eg., cyclohexanone and the like).

To maximize control over the release process, it is desirable to have a polymeric system which degrades only from the surface and deters the permeation of the drug molecules. Achieving such a heterogeneous degradation requires the rate of hydrolytic degradation on the surface to be much faster than the rate of water penetration into the bulk. The ideal polymer would have a hydrophobic backbone, but with a water labile linkage.

EXAMPLE 4

Glioblastoma multiforme is a type of brain cancer that afflicts 14,000 patients in the U.S. each year. Patients with advanced forms of the disease have a life expectancy of less than one year after diagnosis. The tumor invariably grows back. The chemotherapy agent used, BCNU (carmustine, 1,3-bis[2-chloroethyl]-1-nitrosourea), has an in vivo systemic half life of approximately 15 minutes; hence very little active drug contacts the tumor site with systemic administration. In a experimental therapy, BCNU is incorporated into the polymer, which is then implanted into the site of the excised tumor. Implantation directly into the brain bypasses the blood brain barrier, thus minimizing systemic drug exposure and maximizing tumor exposure. The polymer protects the labile BCNU from degradation before it is released, allowing more active BCNU to contact the tumor site. Finally, release occurs over an extended period of several days to several weeks, giving a greater opportunity for the drug to destroy remaining tumor cells.

A fibrous mat of polymers plus 10% drug (BCNU) using the procedure of Example 1 is useful.

In practice, a low spinning temperature (30–40° C. or lower) using either a 25–75 HPC-PCC copolymers or a 20–80 HPC-CL copolymer provides desirable results. The fibrous mat would be placed in the brain near to the tumor to destroy the tumor in a week or two.

EXAMPLE 5

10 g. of CC and 50ml of dry toluene are added to an eight ounce cappable bottle which is then capped with a two hole cap with a self-sealing rubber liner. Nitrogen was then sparged through the free space for twenty minutes to remove all air. The bottle was then pressured with 15 psi of nitrogen after which 5 ml of ethylene oxide (EO) is injected. The bottle is then placed on a rotating rack in a 50° C. water bath and an amount of diethyl zinc (0.91 M in hexane) injected to give a monomer to catalyst molar ratio of 76 and is then tumbled for four hours. Shorstopped with 5 ml ethanol. Copolymer recovered by ethanol precipitation, washed with ethanol and dried in vacuo. The product (4 g) analyzed 40% EO with inherent viscosity of 3.0 (0.1%, in dimethyl acetamide) at 30° C.

The blocking group from this CC-EO copolymer was replaced with hydroxyl by the same procedure described for HPC. Inherent viscosity in DMAC was 0.9 at 30° C. This product was very useful as a pain control agent when admixed with 10% lidocaine or other anaesthetic. It can be distributed in an open wound just prior to closure by a number of methods.

1. As a water dispersion of the lidocaine in the polymer aqueous solution by adding with vigorous agitation a solution of lidocaine in ethanol to the aqueous polymer solution.

2. A water soluble anaesthetic is added to the polymer water solution and then sprayed in the wound as such.

3. The dry lidocaine-polymer mixture is recovered, dissolved in DMF and then spun into a fiber which after recovering in dry form is converted to a fibrous mat which is placed directly in the wound.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A hydroxy-protected carbonate monomer having the structure:

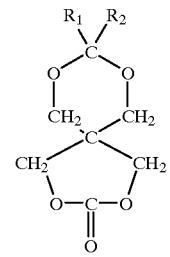

in which $R_1$ is selected from the group consisting of alkyl, cycloalkyl, aryl, alkylaryl, arylalkyl and H; and $R_2$ is selected from the group consisting of alkyl, cycloalkyl, aryl, alkyaryl, arylalkyl and H.

2. Hydroxypolycarbonates for chemically bonding drugs, nucleic acids, proteins and carbohydrate polymers to facilitate their delivery in mammalian systems, said hydroxypolycarbonates having the structure:

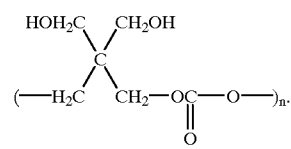

3. A cyclic carbonate polymer having protected hydroxyl groups wherein H of the hydroxy group is replaced with an acetal, ketal, formal or trimethylsilyl group, said carbonate polymer having the structure:

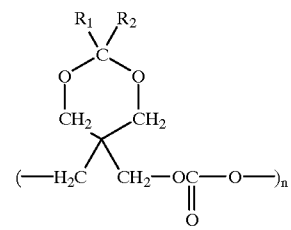

wherein
  $R_1$ is selected from the group consisting of alkyl, cycloalkyl, aryl, alkylaryl, arylalkyl and H;
  $R_2$ is selected from the group consisting of alkyl, cycloalkyl, aryl, alkylaryl, arylalkyl and H n=1–30.

4. A hydroxypolycarbonate according to claim 2 derived from 5,5-bis(hydroxymethyl) 1,3,-dioxan-2-one.

5. A protected cyclic carbonate polmer according to claim 3 in which $R_1$ is $CH_3$ and $R_2$ is $CH_3$.

6. A hydroxy-protected cyclic carbonate monomer according to claim 1 copolymerized with a monomer selected from the group consisting of oxetane, lactide, caprolactone, alkyleneoxide, trimethylene carbonated, and glycolide.

7. A hydroxy-protected cyclic carbonate monomer according to claim 1 in which $R_1$ is $CH_3$ and $R_2$ is $CH_3$.

8. A hydroxy-protected cyclic monomer according to claim 1.

9. The method of synthesizing poly[5,5-bis (hydroxymethyl)-1,3dioxan-2one] comprising reacting pentaerythritol with a compound selected from the group consisting of an acetal, a ketal, a formal and a trimethylsilyl source to replace the hydrogen from each of two hydroxyl groups in said pentaerythritol with a hydroxy protecting group; admixing another compound therewith to convert the remaining two hydroxyls of said pentaerythritol to a cyclic carbonate; purifying and polymerizing said resulting cyclic carbonate; and removing the hydroxy protecting groups to form poly[5,5-bis-(hydroxymethyl)-1-3-dioxan-2-one].

10. A hydroxy-protected cyclic—carbonate copolymer produced according to claim 6.

11. A hydroxypolycarbonate containing ethylene oxide units prepared by removing the protecting group by hydrolysis from the product of claim 8.

* * * * *